US012778697B2

(12) United States Patent
Tadano et al.

(10) Patent No.: US 12,778,697 B2
(45) Date of Patent: Nov. 3, 2026

(54) SURGICAL ROBOT AND CONTROLLER FOR SURGICAL ROBOT

(71) Applicant: RIVERFIELD INC., Tokyo (JP)

(72) Inventors: Kotaro Tadano, Tokyo (JP); Masao Kanazawa, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 85 days.

(21) Appl. No.: 19/042,321

(22) Filed: Jan. 31, 2025

(65) Prior Publication Data

US 2025/0177071 A1 Jun. 5, 2025

Related U.S. Application Data

(63) Continuation of application No. PCT/JP2022/031775, filed on Aug. 23, 2022.

(51) Int. Cl.
*G06F 19/00* (2018.01)
*A61B 34/37* (2016.01)
*A61B 90/00* (2016.01)
*G16H 40/63* (2018.01)

(52) U.S. Cl.
CPC .............. *A61B 34/37* (2016.02); *A61B 90/37* (2016.02); *G16H 40/63* (2018.01)

(58) Field of Classification Search
CPC ......... A61B 34/37; A61B 90/37; A61B 34/76; A61B 34/77; G16H 40/63; G05B 2219/40144; B25J 3/04; B25J 13/025; B25J 9/1689
See application file for complete search history.

(56) References Cited

U.S. PATENT DOCUMENTS

| | | | | |
|---|---|---|---|---|
| 5,631,973 | A * | 5/1997 | Green | H04N 13/337 382/128 |
| 6,120,433 | A | 9/2000 | Mizuno et al. | |
| 6,331,181 | B1 * | 12/2001 | Tierney | G16H 40/63 606/130 |
| 6,424,885 | B1 * | 7/2002 | Niemeyer | A61B 34/77 600/109 |
| 11,701,770 | B2 | 7/2023 | Hashimoto et al. | |
| 2013/0312563 | A1 | 11/2013 | Kawashima et al. | |
| 2015/0018841 | A1 | 1/2015 | Seo | |

(Continued)

FOREIGN PATENT DOCUMENTS

| | | |
|---|---|---|
| JP | 08-71072 A | 3/1996 |
| JP | 10-29177 A | 2/1998 |

(Continued)

*Primary Examiner* — Masud Ahmed
(74) *Attorney, Agent, or Firm* — Sughrue Mion, PLLC

(57) ABSTRACT

A surgical robot includes a master, a master controller, a slave, and a slave controller. The slave controller calculates a slave control value based on a target state and a surgical tool state, the slave control value being for controlling a surgical tool, the target state being a state of the surgical tool based on an operation received by the master, the slave controller controlling the slave based on the slave control value. The master controller calculates a master control value based on the surgical tool state, the target state, and the slave control value obtained from the slave controller, the master control value being for controlling the reaction force, the master controller controlling the master based on the master control value.

20 Claims, 5 Drawing Sheets

(56) References Cited

U.S. PATENT DOCUMENTS

| | | | | |
|---|---|---|---|---|
| 2017/0050310 | A1 | 2/2017 | Kanaoka | |
| 2020/0237456 | A1 | 7/2020 | Prisco et al. | |
| 2025/0177071 | A1 * | 6/2025 | Tadano .................. | A61B 34/76 |

FOREIGN PATENT DOCUMENTS

| | | | |
|---|---|---|---|
| JP | 2009-285099 | A | 12/2009 |
| JP | 7049069 | B2 | 4/2022 |

* cited by examiner

SURGICAL ROBOT AND CONTROLLER FOR SURGICAL ROBOT

CROSS REFERENCE TO RELATED APPLICATION

This application is a continuation application of International Patent Application No. PCT/JP2022/031775 filed on Aug. 23, 2022, the contents of which being incorporated by reference herein in its entirety.

BACKGROUND

The present disclosure relates to a master-slave type surgical robot.

The master-slave type surgical robot receives an operation from a medical worker such as a doctor (hereinafter, referred to as "user") in a master, and uses a surgical tool that is an instrument for surgery, such as a pair of forceps or a scalpel, as a slave. The slave is controlled according to the operation received in the master, and surgery is performed on a patient (hereinafter, referred to as "subject"). A technique is known in which, in such a surgical robot, a force received by the surgical tool during surgery is returned from the slave to the master through a bilateral control, thereby providing force feedback to the user.

SUMMARY

It is an aspect to improve a sensitivity of the force feedback.

According to an aspect of one or more embodiments, there is provided a surgical robot comprising a master configured to receive an operation from a user and to apply a reaction force to the user performing the operation; a master controller configured to control the master and to cause the reaction force to be generated; a slave configured to actuate a surgical tool; a slave controller configured to control the slave based on a target state, the target state being a state of the surgical tool based on the operation received by the master, the slave controller being configured to cause the surgical tool to be actuated; and a slave detector configured to detect a surgical tool state that is a state of the surgical tool. The slave controller is configured to calculate a slave control value based on the surgical tool state and the target state, the slave control value being for controlling the surgical tool, the slave controller being configured to control the slave based on the slave control value, and the master controller is configured to calculate a master control value based on the surgical tool state, the target state, and the slave control value obtained from the slave controller, the master control value being for controlling the reaction force, the master controller being configured to control the master based on the master control value.

According to another aspect of one or more embodiments, there is provided a controller for a surgical robot, the controller comprising a master controller configured to control a master, the master being configured to receive an operation from a user and to apply a reaction force to the user performing the operation and the master controller being configured to cause the reaction force to be generated; and a slave controller configured to control a slave based on a target state, the slave being configured to actuate a surgical tool, the target state being a state of the surgical tool based on the operation received by the master, and the slave controller being configured to cause the surgical tool to be actuated. The slave controller is configured to calculate a slave control value based on a surgical tool state and the target state, the slave control value being for controlling the surgical tool, the surgical tool state being a state of the surgical tool detected by a slave detector, and the slave controller being configured to control the slave based on the slave control value, and the master controller is configured to calculate a master control value based on the surgical tool state, the target state, and the slave control value obtained from the slave controller, the master control value being for controlling the reaction force and the master controller being configured to control the master based on the master control value.

According to yet another aspect of one or more embodiments, there is provided a surgical robot comprising a master configured to receive an operation from a user and to apply a reaction force to the user; a master controller configured to control the master; a slave configured to actuate a surgical tool; a slave controller configured to control the slave to actuate the surgical tool according to a slave driving force; and a slave detector configured to detect a surgical tool state of the surgical tool. The master controller and the slave controller are configured to perform asymmetrical bilateral control based on both proportional control and integral control.

DETAILED DESCRIPTION

Figure 1:
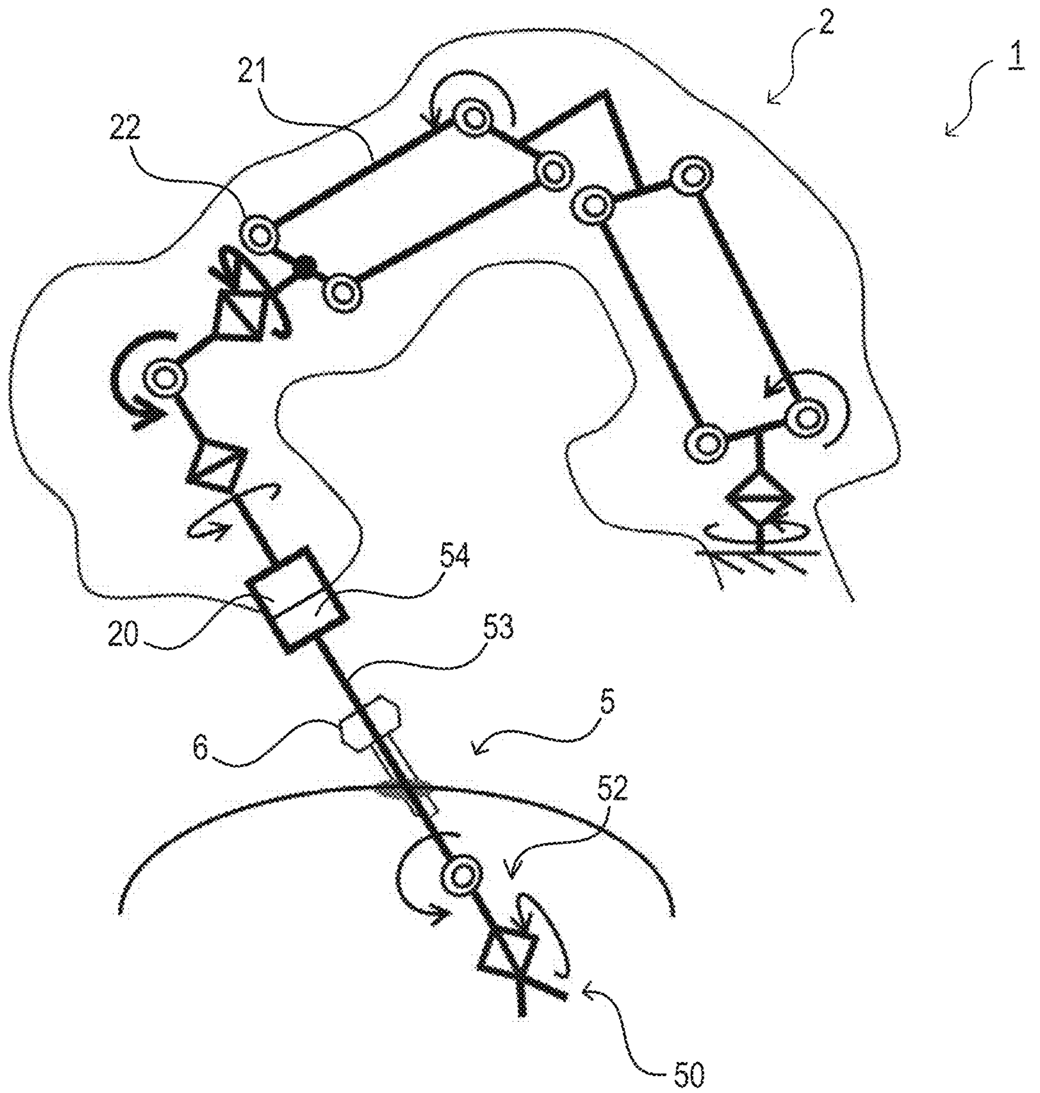
FIG. 1 is a diagram illustrating a surgical robot, according to some embodiments.

In the master and the slave of the surgical robot that performs force feedback, a proportional control is performed. In order to improve the sensitivity of the force feedback, it is conceivable that a gain of the proportional control of the master is increased.

However, for example, if a wire for transmitting a driving force to the surgical tool is slack, and/or there is a gap between the surgical tool and a transmission structure of the driving force, and/or there is a delay in the control, an excessive increase in the gain of the proportional control of the master may cause difficulty in controlling the surgical tool. Therefore, there is a limit to the ability to increase the gain of the proportional control.

It is an aspect to improve the sensitivity of the force feedback.

According to some embodiments, a surgical robot may include a master, a master controller, a slave, a slave controller, and a slave detector. The master may be configured to receive an operation from a user and to apply a reaction force to the user performing the operation. The master controller may be configured to control the master and to cause the reaction force to be generated. The slave may be configured to actuate a surgical tool. The slave controller may be configured to control the slave based on a target state, the target state being a state of the surgical tool based on the operation received by the master, the slave controller being configured to cause the surgical tool to be actuated. The slave detector may be configured to detect a surgical tool state that is a state of the surgical tool. The slave controller may be configured to calculate a slave control value based on the surgical tool state and the target state, the slave control value being for controlling the surgical tool, the slave controller being configured to control the slave based on the slave control value. The master controller may be configured to calculate a master control value based on the surgical tool state, the target state, and the slave control value obtained from the slave controller, the master control value being for controlling the reaction force, the master controller being configured to control the master based on the master control value.

In the above configuration, the master control value is calculated by taking the slave control value into consideration, and the reaction force to the user is controlled by the master control value. This configuration and operation allows the changes in the slave control value to be reflected more quickly in the master control value, and as a result, the sensitivity of the force feedback improves.

In some embodiments, the slave controller may be configured to calculate the slave control value by performing an integration based on the surgical tool state and the target state.

In the above configuration, a disturbance (in other words, a steady-state error) in the slave controller can be reduced. Therefore, it is possible to calculate the slave control value more accurately.

In some embodiments, the slave controller may be configured to calculate the slave control value by a proportional control based on a difference between the surgical tool state and the target state. The master controller may be configured to calculate the master control value by a proportional control based on the difference between the surgical tool state and the target state. A gain of the proportional control in the master controller may be greater than a gain of the proportional control in the slave controller.

In the above configuration, the sensitivity of the force feedback may be improved.

In some embodiments, the master controller may be configured to calculate the master control value by a proportional control based on a difference between the surgical tool state and the target state. The surgical robot may further include a display and an input section. The display may be configured to display a gain of the proportional control. The input section may be configured to receive an operation to change the gain of the proportional control.

In the above configuration, the sensitivity of the force feedback may be adjusted.

In some embodiments, the slave controller may be configured to calculate the slave control value by a proportional control based on a difference between the surgical tool state and the target state. The surgical robot may further include a display and an input section. The display may be configured to display a gain of the proportional control. The input section may be configured to receive an operation to change the gain of the proportional control.

The above configuration allows customization for better control of the surgical tool.

In some embodiments, the slave controller may be configured to calculate the slave control value by further performing an integral control based on the difference between the surgical tool state and the target state. The display may be configured to further display a gain of the integral control. The input section may be configured to further receive an operation to change the gain of the integral control.

The above configuration allows customization for better control of the surgical tool.

According to some embodiments, a controller for a surgical robot may include a master controller and a slave controller. The master controller may be configured to control a master, the master being configured to receive an operation from a user and to apply a reaction force to the user performing the operation, the master controller being configured to cause the reaction force to be generated. The slave controller may be configured to control a slave based on a target state, the slave being configured to actuate a surgical tool, the target state being a state of the surgical tool based on the operation received by the master, the slave controller being configured to cause the surgical tool to be actuated. The slave controller may be also configured to calculate a slave control value based on a surgical tool state and the target state, the slave control value being for controlling the surgical tool, the surgical tool state being a state of the surgical tool detected by a slave detector, the slave controller being configured to control the slave based on the slave control value. The master controller may be configured to calculate a master control value based on the surgical tool state, the target state, and the slave control value obtained from the slave controller, the master control value being for controlling the reaction force, the master controller being configured to control the master based on the master control value.

In the above configuration, the master control value is calculated by taking the slave control value into consideration, and the reaction force to the user is controlled by the master control value. This configuration and operation allows the changes in the slave control value to be reflected more quickly in the master control value and, as a result, the sensitivity of the force feedback improves.

Hereinafter, various embodiments are described with reference to the drawings. It should be noted that the various embodiments are not limited in any way to the following embodiments, and may take various forms as long as those forms fall within the technical scope of the present disclosure and the appended claims.

Figure 2:
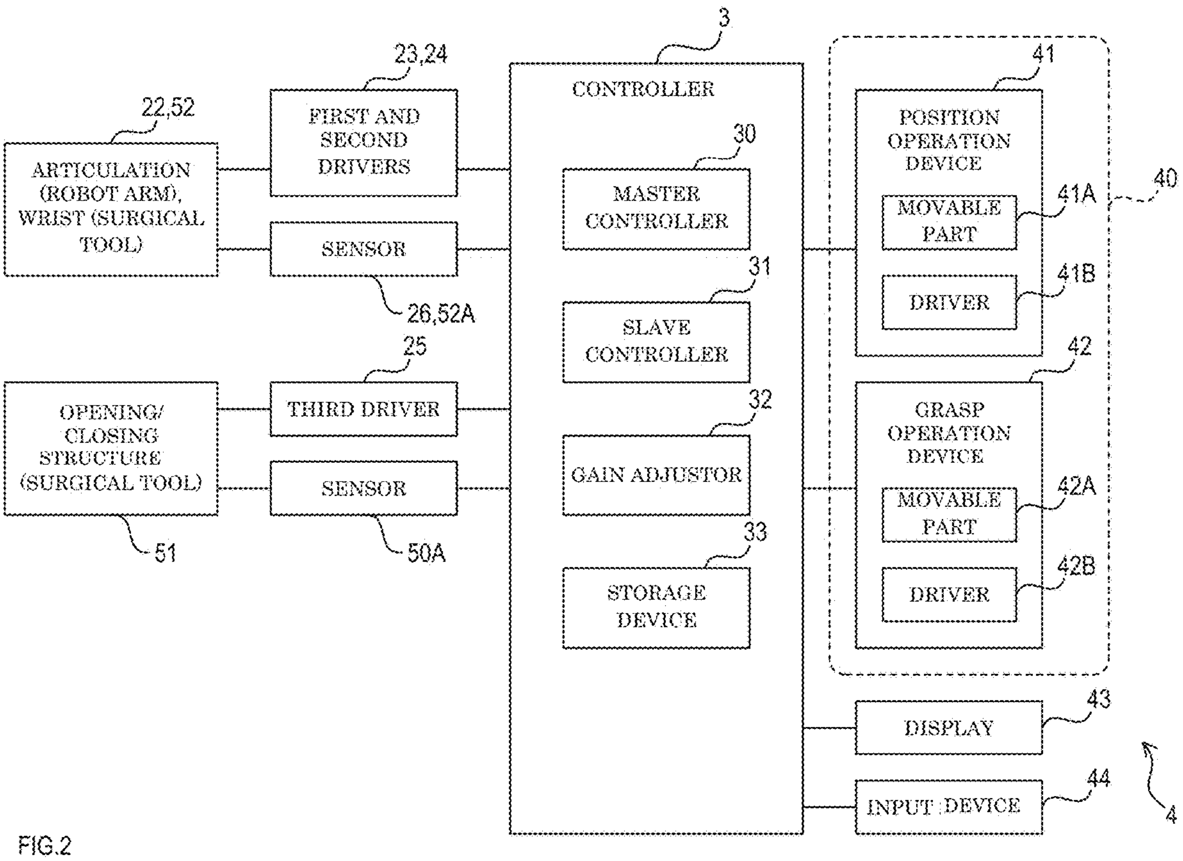
FIG. 2 is a block diagram of the surgical robot, according to some embodiments.

FIG. 1 is a diagram illustrating a surgical robot, according to some embodiments, and FIG. 2 is a block diagram of the surgical robot, according to some embodiments. As illustrated in FIGS. 1 and 2, a surgical robot 1 may include two robot arms 2 having the same configuration, a controller (control unit) 3, and an operation structure 4. Each of the robot arms 2 is equipped with a surgical tool 5. It should be noted that the number of robot arms 2 may be one, or three or more.

The surgical robot 1 is configured as a master-slave type robot system. The surgical robot 1 actuates the robot arm 2 and the surgical tool 5 (i.e., a slave) that moves in response to the user operating an operation section of the operation structure 4 (i.e., a master) to thereby perform surgery on a subject. The surgical robot 1 is configured to perform force feedback. As described in detail below, during surgery, the surgical robot 1 is configured to allow the user to perceive a force received by the surgical tool actuated in accordance with the user's operation through the operation section of the operation structure 4.

The surgical tool 5 is configured such that a tip of a distal end of the surgical tool 5 is inserted into the subject's body through a trocar 6 punctured in the subject's abdomen or the like, and a part provided at the tip is actuated within the body, thereby performing a surgical treatment (see FIG. 1). In an embodiment, as an example, a pair of forceps is used as the surgical tool 5. However, embodiments are not limited thereto and, in some embodiments, a surgical tool other than the forceps, such as a scalpel, may also be used.

The surgical tool 5 includes a grasper 50, an opening/closing structure 51, a wrist 52, a shaft 53, and an adapter 54 (see FIGS. 1 and 2).

The shaft 53 is an elongated cylindrical portion and provided with an adapter 54 at the end opposite the tip of the surgical tool 5.

The grasper 50 is provided at the tip of the shaft 53 and inserted through the trocar 6 into the subject's body to perform a treatment, such as grasping the subject's internal tissues. The grasper 50 includes a first portion and a second portion and the opening/closing structure 51, and the opening/closing structure 51 is configured to move the first and second portions closer together and farther apart (hereinafter, also referred to as "opening/closing movement"). The first and second portions move closer together to thereby grasp an object, and the grasped object is released by the first and second portions moving apart.

The grasper 50 includes a sensor 50A for detecting the state of the opening/closing movement (hereinafter, referred to as "opening/closing state") (see FIG. 2). Specifically, for example, the sensor 50A may detect a distance between the first portion and the second portion, and/or detect an angle between the first portion and the second portion as the opening/closing state.

The wrist 52 is provided near the grasper 50 in the shaft 53, and is rotatable at one or more locations, and changes the orientation (i.e., posture) of the grasper 50 by rotating at the location. The wrist 52 includes a sensor 52A for detecting the orientation of the grasper 50.

The sensors 50A, 52A output sensor signals indicating detection results to the controller 3.

The cylindrical shaft 53 contains a plurality of wires that transmits a driving force to the grasper 50 and the wrist 52 to actuate the grasper 50 and the wrist 52.

The robot arm 2 is configured to hold the surgical tool 5, which is mounted on a tip of the robot arm 2, at a specified position and to change the posture of the robot arm 2 in response to the user's operation to thereby adjust the position and orientation (i.e., posture) of the surgical tool 5 (see FIG. 1).

The tip of the robot arm 2 is provided with a connector 20 that may be attached to and detached from an adapter 54 of the surgical tool 5, and the surgical tool 5 is mounted through the connector 20. Various types of forceps and surgical tools other than forceps can be mounted on the connector 20 of the robot arm 2.

The robot arm 2 is configured as a link structure, and includes two or more arms 21 and two or more articulations 22 (i.e., joints) that are provided at the ends of the arms 21 and that rotate each arm 21. Each arm 21 is coupled to another arm 21 through the articulation 22.

The robot arm 2 includes a first driver 23, a second driver 24, and a third driver 25 (see FIG. 2). The first to third drivers 23-25 may include, for example, at least one pneumatic actuator, at least one motor, and/or the like.

The first driver 23 is configured to drive each articulation 22 in response to the user's operation, and the driving force generated by the first driver 23 is transmitted to each articulation 22 through a transmission structure including a plurality of wires and a plurality of pulleys. The first driver 23 drives each articulation 22 to thereby displace each arm 21 and change the posture of the robot arm 2, thereby changing the orientation and position of the surgical tool 5.

The second driver 24 is configured to drive the wrist 52 of the surgical tool 5 in response to the user's operation, and the driving force generated by the second driver 24 is transmitted to the wrist 52 through the transmission structure. The second driver 24 drives the wrist 52, thereby changing the orientation of the grasper 50.

The third driver 25 is configured to drive the opening/closing structure 51 of the surgical tool 5 in response to the user's operation, and the driving force generated by the third driver 25 is transmitted to the opening/closing structure 51 through the transmission structure. The third driver 25 drives the opening/closing structure 51, thereby changing the opening/closing state of the grasper 50.

The robot arm 2 includes a sensor 26 for detecting the posture of the robot arm 2. The sensor 26 may detect, for example, an angle at which each articulation 22 rotates, or a state (e.g., compressed air pressure) of the first driver 23 driving each articulation 22. The sensor 26 also outputs a sensor signal indicating the detection result to the controller 3.

The operation structure 4 is configured to receive operations of the robot arm 2 and the surgical tool 5 from the user and includes two operation devices 40 corresponding to the two robot arms 2, a display 43, and an input device 44 (see FIG. 2). Each operation device 40 includes a position operation device 41 and a grasp operation device 42.

The position operation device 41 receives an operation for adjusting the position and orientation of the grasper 50 of the surgical tool 5, which is mounted on the robot arm 2 corresponding to the operation device 40 provided with the position operation device 41. That is, in response to the operation applied to the position operation device 41, the posture of the robot arm 2 is changed to thereby adjust the position and orientation of the surgical tool 5 and the wrist 52 of the surgical tool 5 is actuated to thereby adjust the orientation of the grasper 50.

The grasp operation device 42 receives an operation to cause the grasper 50 of the surgical tool 5, which is mounted on the robot arm 2 corresponding to the operation device 40 provided with the grasp operation device 42, to perform the opening/closing movement.

Then, the operation device 40 outputs, to the controller 3, an operation signal indicating the contents of the operations received by the position operation device 41 and the grasp operation device 42.

As described above, the surgical robot 1 is configured to perform force feedback. Thus, the position operation device 41 and the grasp operation device 42 provide the user with a reaction force corresponding to a force received by the surgical tool 5 from the subject or the like when the surgical tool 5 is actuated in accordance with the user's operation.

Specifically, the position operation device 41 includes a movable part 41A and a driver 41B, and the grasp operation device 42 includes a movable part 42A and a driver 42B. The drivers 41B, 42B drive the movable parts 41A, 42A by, for example, a pneumatic actuator, a motor, or the like. The driver 41B of the position operation device 41 displaces the movable part 41A in accordance with the control signal input from the controller 3, thereby providing the reaction force to the user operating the position operation device 41. Similarly, the driver 42B of the grasp operation device 42 displaces the movable part 42A in accordance with the control signal input from the controller 3, thereby providing the reaction force to the user operating the grasp operation device 42.

The display 43 is configured as a liquid crystal display, for example, and is driven in accordance with a control signal from the controller 3 to display, for example, a setting screen, an endoscope image of the subject, a state of the robot arm 2 and a state of the surgical tool 5, and information used for operating the surgical robot 1. The endoscope image may be, for example, an image of the patient's body cavity obtained from an endoscope inserted into the patient's body cavity through another trocar punctured in the patient's abdomen or the like. The endoscope inserted into the patient's body cavity through another trocar may be held by another robot arm or an endoscope holding device that is not shown.

The input device 44 may receive an operation from the user and the like, and includes, for example, a keyboard, a mouse, a touch panel, a foot switch, and/or the like. The input device 44 outputs an operation signal indicating the content of the received operation to the controller 3.

The controller 3 is configured to control each robot arm 2, each surgical tool 5, and the operation structure 4 (see FIG. 2). The controller 3 is configured as a computer system equipped with a processor, ROM, RAM, a bus, an input/output section, and the like. The functions of the controller 3 are realized by the processor executing a program stored in the ROM or the RAM to cause the processor to execute the functions of the controller 3. Some or all of the functions realized by the processor may be realized by hardware, such as hardware control logic, at least one IC and/or the like.

The controller 3 includes a master controller 30, a slave controller 31, a gain adjustor 32, and a storage device 33.

The storage device 33 is a non-volatile storage medium, such as a hard disk and a flash memory, and stores the program that is executed by the controller 3 and information about the operation of the surgical robot 1.

Here, the functions of the master controller 30 and the slave controller 31 are realized by execution of the processor. The master controller 30 is configured to control the operation structure 4, and the slave controller 31 is configured to control each robot arm 2 and the surgical tool 5 mounted on each robot arm 2. As described in detail below, the master controller 30 and the slave controller 31 perform a master-slave control to thereby calculate a master driving force τm (i.e., master control value) and a slave driving force τs (i.e., a slave control value).

The master driving force τm represents the driving forces of the drivers 41B, 42B of the position operation device 41 and the grasp operation device 42 in each operation device 40 of the operation structure 4. The slave driving force τs represents the driving forces of the first to third drivers 23-25 in each robot arm 2.

The master controller 30 outputs control signals to the drivers 41B, 42B of the position operation device 41 and the grasp operation device 42, and controls the drivers 41B, 42B to respectively actuate the movable parts 41A, 42A with the driving forces τm, thereby generating the reaction forces.

The master controller 30 detects the operations performed by the user on the position operation device 41 and the grasp operation device 42 based on operation signals from the operation structure 4. The master controller 30 then determines a target state (i.e., Xm) regarding the current position and orientation and the opening/closing movement of the grasper 50 based on the detected operations. The details of the target state and Xm are described below.

The slave controller 31 outputs control signals to the first to third drivers 23-25 of the robot arm 2. Thus, the slave controller 31 controls the first and the second drivers 23, 24 to actuate the plurality of articulations 22 and the wrist 52 with the driving forces τs. The slave controller 31 controls the third driver 25 to actuate the opening/closing structure 51 with the driving force τs.

The slave controller 31 determines a current state of the opening/closing movement of the grasper 50 as a surgical tool state (i.e., Xs) based on a sensor signal from the sensor 50A provided to the grasper 50 of the surgical tool 5. The slave controller 31 determines the current position and orientation of the grasper 50 as the surgical tool state (i.e., Xs) based on a sensor signal from the sensor 52A provided to the wrist 52 of the surgical tool 5 and a sensor signal from the sensor 26 provided to the robot arm 2. The details of the surgical tool state and Xs are described below.

Figure 3:
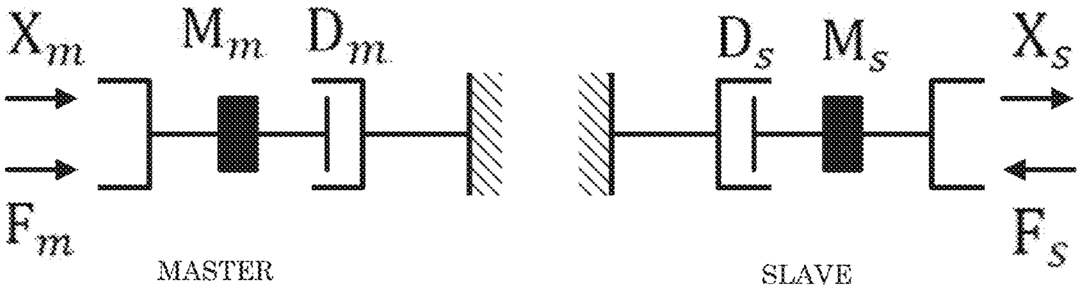
FIG. 3 is a diagram illustrating a master-slave modeled in a one-degree-of-freedom system, according to some embodiments.

The master and the slave of an embodiment may be modeled as a one-degree-of-freedom system shown in FIG. 3. The dynamics of the master and the slave are represented by the following equations.

[Mathematical 1]

$$\tau_m + F_m = M_m \ddot{X}_m + D_m \dot{X}_m \quad (1)$$

[Mathematical 2]

$$\tau_s - F_s = M_s \ddot{X}_s + D_s \dot{X}_s \quad (2)$$

In the control of the position and orientation of the grasper 50, the position operation device 41 used for operations corresponds to the master, and the grasper 50 corresponds to the slave. In the control of the opening/closing movement of the grasper 50, the grasp operation device 42 used for operations corresponds to the master, and the grasper 50 corresponds to the slave.

Xm represents a state to be achieved by the slave (i.e., a target state of the slave) determined based on a current state of the master determined by the operation from the user. More specifically, the target state corresponds to target values of the position and orientation of the grasper 50 and a target value of the opening/closing state. Mm represents the mass of the master, Dm represents a viscous friction coefficient of a damper on the master side, and Fm represents an external force applied to the master by the user's operation. As described above, τm represents the driving force when the driver actuates the movable part to generate the reaction force in the position operation device 41 and the grasp operation device 42.

Xs represents a current state of the slave (i.e., a surgical tool state). More specifically, the surgical tool state corresponds to values indicating the current position and orientation of the grasper 50 and a value indicating the current opening/closing state. Ms represents the mass of the slave, Ds represents a viscous friction coefficient of a damper on the slave side, and Fs represents an external force applied to the slave by the subject during actuation. As described above, τs represents the driving forces when the first and second drivers 23, 24 actuate the articulation 22 and the wrist 52 to cause the position and orientation of the grasper 50 to achieve the target state. In addition, τs also represents the driving force when the third driver 25 actuates the opening/closing structure 51 to cause the opening/closing state of the grasper 50 to achieve the target state.

Figure 4:
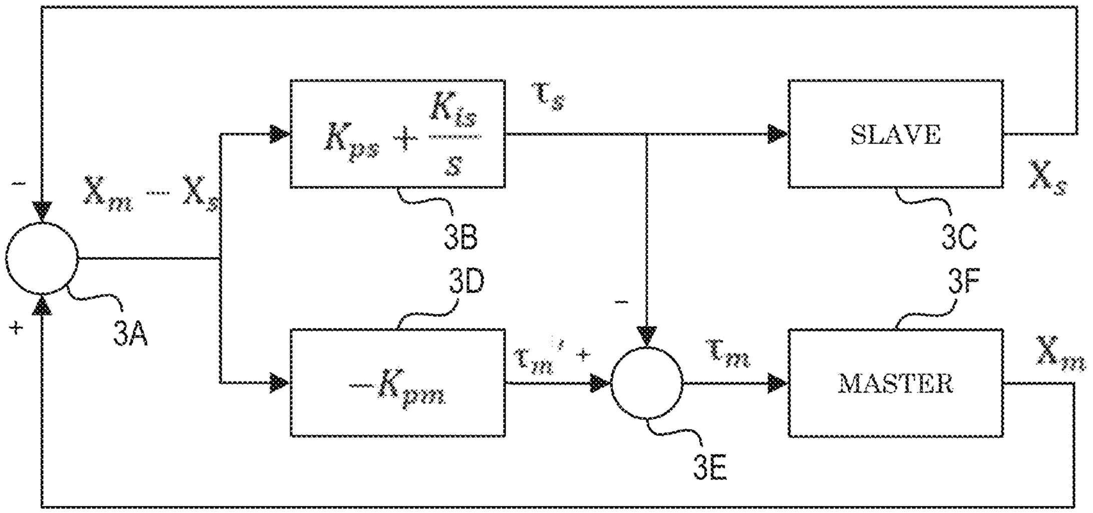
FIG. 4 is a block diagram of an asymmetric bilateral control, according to some embodiments.

The master controller 30 and the slave controller 31 perform asymmetric bilateral control as shown in the block diagram of FIG. 4. In this control, Xs is subtracted from Xm at a summing point 3A to calculate a difference, and the difference is input to a transfer element 3B. The transfer element 3B calculates a slave driving force τs by a proportional control and an integral control based on the difference and outputs the driving force τs to both a transfer element 3C representing the slave and a summing point 3E. The transfer element 3C outputs Xs to the summing point 3A.

The difference between Xm and Xs calculated at the summing point 3A is also input to a transfer element 3D that performs the proportional control, and the transfer element 3D calculates τm' by the proportional control based on the difference and outputs τm' to the summing point 3E. At the summing point 3E, the slave driving force τs is subtracted from τm' to calculate a master driving force τm, and the driving force τm is output to a transfer element 3F representing the master. The transfer element 3F outputs Xm to the summing point 3A.

The transfer element 3B corresponds to a process in the slave controller 31, and performs the proportional control with a gain Kps and the integral control with a gain Kis. The transfer element 3D and the summing point 3E correspond to processes in the master controller 30, and the transfer element 3D performs the proportional control with a gain −Kpm.

That is, the master controller 30 calculates the master driving force τm based on Xm, Xs, and the slave driving force τs obtained from the slave controller 31. The absolute value of −Kpm (hereinafter, |Kpm|) is greater than the absolute value of Kps (hereinafter, |Kps|). More specifically, as an example, |Kpm| may be two times or more and three times or less than |Kps|. However, |Kpm| and |Kps| are not limited thereto, and may be determined as appropriate. For example, |Kpm| may be smaller than |Kps|.

A driving force μm after scaling may be input into the transfer element 3F representing the master. The term "scaling" means multiplying the master driving force τm by a coefficient of a specified value greater than 1. This scaling allows a reaction force greater than the force received by the slave to be applied to the user, and allows the user to appropriately perform a treatment on a minute part of the subject's body and a treatment that requires precision.

The block diagram of FIG. 3 is represented by the following equations (3) and (4)

[Mathematical 3]

$$\tau_m = (K_{pm} + K_{ps})(X_s - X_m) + K_{is}\int (X_s - X_m)dt \tag{3}$$

[Mathematical 4]

$$\tau_s = K_{ps}(X_m - X_s) + K_{is}\int (X_m - X_s)dt \tag{4}$$

By substituting the equations (3) and (4) into the equations (1) and (2) and by performing a Laplace transformation, the following equation (5) may be obtained.

[Mathematical 5]

$$\begin{aligned} F_m(s) = M_mX_ms^2 + D_mX_ms - \tau_m = \\ M_mX_ms^2 + D_mX_ms + \left(K_{pm} + K_{ps} + \frac{K_{is}}{s}\right)(X_m - X_s) = \\ M_mX_ms^2 + D_mX_ms + G(s)\left(M_s\ddot{X}_s + D_s\dot{X}_s + F_s\right) \end{aligned} \tag{5}$$

Note that G(s) satisfies the following equation (6).

[Mathematical 6]

$$G(s) = \frac{(K_{pm} + K_{ps}) + K_{is}}{K_{pm}s + K_{is}} \tag{6}$$

If T and a satisfy equations (7) and (8), an equation (9) holds.

[Mathematical 7]

$$T = \frac{K_{ps}}{K_{is}} \tag{7}$$

[Mathematical 8]

$$a = \frac{K_{pm} + K_{ps}}{K_{ps}} \tag{8}$$

[Mathematical 9]

$$G(s) = \frac{1 + saT}{1 + sT} \tag{9}$$

That is, the equation (9) shows that the asymmetric bilateral control has phase-lead compensation characteristics. Thus, by setting the gain |Kpm| of the proportional control of the master greater than the gain |Kps| of the proportional control of the slave, a gain of G(s) is "a" in a high-frequency range and "1" in a low-frequency range. That is, when the external force Fs applied to the slave changes significantly, such as at the moment when the slave comes in contact with an object, a force multiplied by "a" is fed back to the master, and a force multiplied by "1" is fed back to the master in a steady state. Therefore, the asymmetric bilateral control promotes both highly accurate slave tracking performance through the integral control and highly sensitive force feedback.

As shown in equations (10) and (11), the acceleration and the velocity are used in each of the equations (3) and (4), whereby an inertial force and a viscous force may be compensated.

[Mathematical 10]

$$\tau_m = (K_{pm} + K_{ps})(X_s - X_m) + K_{is}\int (X_s - X_m)dt + \left(M_m\ddot{X}_m + D_m\dot{X}_m\right) \tag{10}$$

[Mathematical 11]

$$\tau_s = K_{ps}(X_m - X_s) + K_{is}\int (X_m - X_s)dt + \left(M_s\ddot{X}_s + D_s\dot{X}_s\right) \tag{11}$$

From the equations (10) and (11), an equation (12) is obtained.

[Mathematical 12]

$$F_m(s) = G(s)F_s \tag{12}$$

From the equation (12), it can be seen that the negative effects of the dynamics of the master and the slave can be reduced by adding compensation as in the equations (10) and (11).

Moreover, although the slave driving force τs is calculated using the proportional control and the integral control in the slave controller 31, the slave driving force τs may be calculated using a disturbance observer in place of the integral control.

In the asymmetric bilateral control, the master controller 30 calculates the master driving force τm by subtracting the slave driving force τs from τm' output from the transfer element 3D. However, the calculation method of τm is not limited thereto, and may be determined as appropriate. Specifically, for example, a specified calculation may be performed based on the slave driving force τs to calculate τs', and τs' may be subtracted from τm' to thereby calculate τm. The specified calculation may involve, for example, multiplying τs by a specified coefficient or adding a specified coefficient to τs. For example, τm may also be calculated by multiplying τm' by τs (or τs'), dividing τm' by τs (or τs'), or adding τs (or τs') to τm'.

In the transfer element 3B, τs may be calculated without using the integral control and the disturbance observer. In the transfer elements 3B and 3D, a derivative control may be further performed to calculate τs and τm', respectively.

The function of the gain adjustor 32 is realized by the processor of the controller 3 (see FIG. 2). The gain adjustor 32 adjusts the gains of the integral control and the proportional control in the asymmetric bilateral control in accordance with the operation received from the user or the like through the input device 44.

That is, the storage device 33 stores the gains Kpm of the proportional control in the master controller 30 and the gains Kps of the proportional control and the gains Kis of the integral control in the slave controller 31 for each robot arm 2. For example, when the surgical robot 1 is started up or the like, the controller 3 reads the gains Kpm, Kps, and Kis corresponding to each robot arm 2 from the storage device 33, and performs the above-described bilateral control using the read gains Kpm, Kps and Kis.

Figure 5:
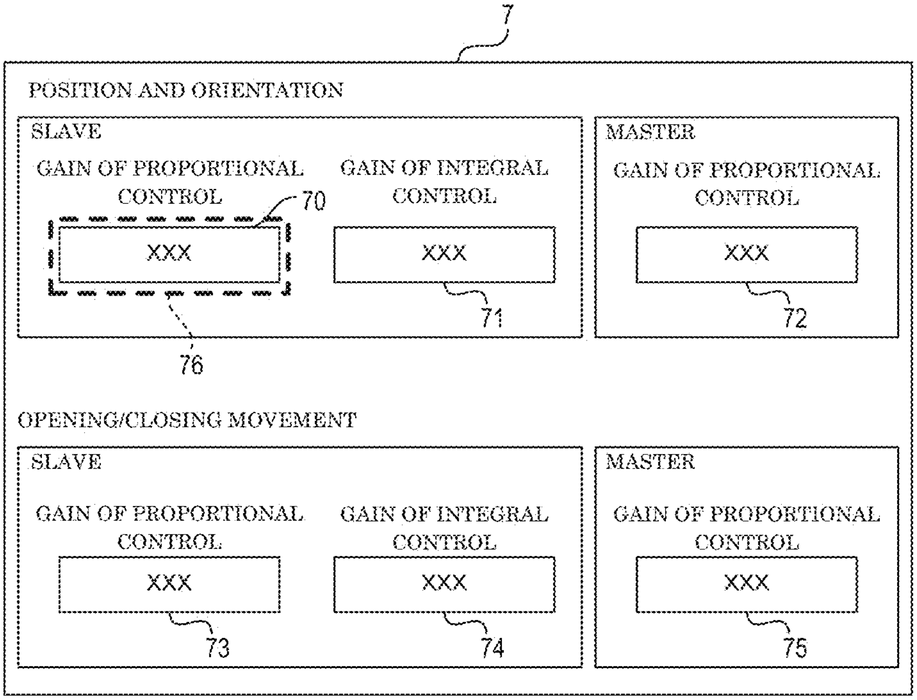
FIG. 5 is a diagram illustrating a gain setting screen, according to some embodiments.

FIG. 5 is a diagram illustrating a gain setting screen, according to some embodiments. When receiving an operation signal indicating an instruction to adjust the gain(s) from the input device 44, the gain adjustor 32 outputs a control signal to the display 43 to show a gain setting screen 7 on the display 43, as illustrated in FIG. 5. The gain setting screen 7 is provided for each robot arm 2, and is used to adjust the gain(s) in the bilateral control of the corresponding robot arm 2. In accordance with an operation signal input from the input device 44, the gain adjustor 32 outputs a control signal to the display 43 to switch the gain setting screen 7 shown on the display 43 to a gain setting screen 7 corresponding to another robot arm 2.

The gain setting screen 7 includes display areas 70, 71 for the gains of the proportional and integral controls of the slave, and a display area 72 for the gain of the proportional control of the master, related to the control of the position and orientation of the grasper 50. The gain setting screen 7 also includes display areas 73, 74 for the gains of the proportional and integral controls of the slave, and a display area 75 for the gain of the proportional control of the master, related to the control of the opening/closing state of the grasper 50. The gain adjustor 32 outputs a control signal to the display 43 to cause these display areas 70-75 to show current values of the gains in the corresponding proportional control or integral control.

The gain setting screen 7 shows a cursor 76 that is superimposed on any one of the display areas 70-75. In accordance with an operation signal input from the input device 44, the gain adjustor 32 selects one of the display areas 70-75 and outputs a control signal to the display 43 to cause it to show the cursor 76 superimposed on the selected display area. In accordance with an operation signal input from the input device 44, the gain adjustor 32 accepts a change to the gain value displayed in the selected display area, and outputs a control signal to the display 43 to cause it to show the changed gain value in the display area.

When an operation signal indicating the confirmation of the gain values is input from the input device 44, the gain adjustor 32 updates the gain values of the proportional control or the integral control corresponding to the display areas 70-75 to the gain values displayed in the display areas. Thereafter, the updated gain values are used in the bilateral control. The gain adjustor 32 stores each updated gain value in the storage device 33.

In a related art bilateral control, a symmetric or force feedback method using the proportional control and the derivative control has been used. In order to improve the accuracy of the control, when forceps are used as a surgical tool, in the related art bilateral control, it is necessary to minimize an error as much as possible even if a large external force (e.g., external force of about 5-20 N) is applied to the tip of the forceps. To this end, it is necessary to increase the gain of the proportional control in the slave control. However, as described above, there is a limit to increasing the gain of the proportional control. Thus, it is necessary to control the slave by an integral-based method, such as the integral control or the disturbance observer. However, introducing such a method may delay the force feedback.

In contrast, in the asymmetric bilateral control according to various embodiments, the slave controller 31 calculates τs by the proportional control and the integral control. Thus, disturbances may be well suppressed in the slave controller 31, and the accuracy of τs improves. The master controller 30 calculates τm based on τs obtained from the slave controller 31, and uses τm to control the reaction force generated in the position operation device 41 and the grasp operation device 42, which serve as the master. Therefore, the sensitivity of the force feedback improves. That is, in various embodiments, even though the slave is controlled by the integral-based method, the delay in the force feedback may be reduced.

The gain |Kpm| of the proportional control of the master is greater than the gain |Kps| of the proportional control of the slave. Therefore, the sensitivity of the force feedback improves.

The gain adjustor 32 adjusts each gain in the bilateral control corresponding to each robot arm in accordance with the operation received through the input device 44. The gain adjustor 32 thus allows the adjustment of the sensitivity of the force feedback and the customization for better control of the surgical tool.

Two or more functions of one element may be achieved by two or more elements, and one function of one element may be achieved by two or more elements. Furthermore, two or more functions of two or more elements may be achieved by one element, and one function achieved by two or more elements may be achieved by one element. In some embodiments, a part of the configurations described above may be omitted. Furthermore, in some embodiments, at least a part of the configurations may be added to or replaced by another configuration.

The position operation device 41 and the grasp operation device 42 of the operation device 40 correspond to examples of the master. The first to third drivers 23-25 of the robot arm 2 correspond to examples of the slave, and the sensor 26 of the robot arm 2 and the sensors 50A, 52A of the surgical tool correspond to examples of the slave detector.

Implementations

[Item 1]

A surgical robot comprising:

a master configured to receive an operation from a user and to apply a reaction force to the user performing the operation;

a master controller configured to control the master and to cause the reaction force to be generated;

a slave configured to actuate a surgical tool;

a slave controller configured to control the slave based on a target state, the target state being a state of the surgical tool based on the operation received by the master, the slave controller being configured to cause the surgical tool to be actuated; and a slave detector configured to detect a surgical tool state that is a state of the surgical tool, wherein the slave controller is configured to calculate a slave control value based on the surgical tool state and the target state, the slave control value being for controlling the surgical tool, the slave controller being configured to control the slave based on the slave control value, and wherein the master controller is configured to calculate a master control value based on the surgical tool state, the target state, and the slave control value obtained from the slave controller, the master control value being for controlling the reaction force, the master controller being configured to control the master based on the master control value.

[Item 2]

The surgical robot according to Item 1, wherein the slave controller is configured to calculate the slave control value by performing an integration based on the surgical tool state and the target state.

[Item 3]

The surgical robot according to Item 1 or 2, wherein the slave controller is configured to calculate the slave control value by a proportional control based on a difference between the surgical tool state and the target state, wherein the master controller is configured to calculate the master control value by a proportional control based on the difference between the surgical tool state and the target state, and wherein a gain of the proportional control in the master controller is greater than a gain of the proportional control in the slave controller.

[Item 4]

The surgical robot according to any one of Items 1 to 3, wherein the master controller is configured to calculate the master control value by a proportional control based on a difference between the surgical tool state and the target state, and wherein the surgical robot further comprises a display configured to display a gain of the proportional control and an input section configured to receive an operation to change the gain of the proportional control.

[Item 5]

The surgical robot according to any one of Items 1 to 4, wherein the slave controller is configured to calculate the slave control value by a proportional control based on a difference between the surgical tool state and the target state, and wherein the surgical robot further comprises a display configured to display a gain of the proportional control and an input section configured to receive an operation to change the gain of the proportional control.

[Item 6]

The surgical robot according to Item 5, wherein the slave controller is configured to calculate the slave control value by further performing an integral control based on the difference between the surgical tool state and the target state, wherein the display is configured to further display a gain of the integral control, and wherein the input section is configured to further receive an operation to change the gain of the integral control.

[Item 7]

A controller for a surgical robot, the controller comprising:

a master controller configured to control a master, the master being configured to receive an operation from a user and to apply a reaction force to the user performing the operation, the master controller being configured to cause the reaction force to be generated; and a slave controller configured to control a slave based on a target state, the slave being configured to actuate a surgical tool, the target state being a state of the surgical tool based on the operation received by the master, the slave controller being configured to cause the surgical tool to be actuated, wherein the slave controller is configured to calculate a slave control value based on a surgical tool state and the target state, the slave control value being for controlling the surgical tool, the surgical tool state being a state of the surgical tool detected by a slave detector, the slave controller being configured to control the slave based on the slave control value, and wherein the master controller is configured to calculate a master control value based on the surgical tool state, the target state, and the slave control value obtained from the slave controller, the master control value being for controlling the reaction force, the master controller being configured to control the master based on the master control value.

While various embodiments have been illustrated and described above with respect to the accompanying drawings, it will be apparent to those skilled in the art that modifications and variations may be made without departing from the scope of the present disclosure as defined by the appended claims.

The invention claimed is:

1. A surgical robot comprising:

a master configured to receive an operation from a user and to apply a reaction force to the user performing the operation;

a master controller configured to control the master and to cause the reaction force to be generated;

a slave configured to actuate a surgical tool;

a slave controller configured to control the slave based on a target state, the target state being a state of the surgical tool based on the operation received by the master, the slave controller being configured to cause the surgical tool to be actuated; and a slave detector configured to detect a surgical tool state that is a state of the surgical tool, wherein the slave controller is configured to calculate a slave control value based on the surgical tool state and the target state, the slave control value being for controlling the surgical tool, the slave controller being configured to control the slave based on the slave control value, and wherein the master controller is configured to calculate a master control value based on the surgical tool state, the target state, and the slave control value obtained from the slave controller, the master control value being for controlling the reaction force, the master controller being configured to control the master based on the master control value.

2. The surgical robot according to claim 1, wherein the slave controller is configured to calculate the slave control value by performing an integration based on the surgical tool state and the target state.

3. The surgical robot according to claim 2, wherein the slave controller is configured to calculate the slave control value by a proportional control based on a difference between the surgical tool state and the target state, wherein the master controller is configured to calculate the master control value by a proportional control based on the difference between the surgical tool state and the target state, and wherein a gain of the proportional control in the master controller is greater than a gain of the proportional control in the slave controller.

4. The surgical robot according to claim 2, wherein the master controller is configured to calculate the master control value by a proportional control based on a difference between the surgical tool state and the target state, and wherein the surgical robot further comprises:

a display configured to display a gain of the proportional control; and an input device configured to receive an operation to change the gain of the proportional control that is displayed.

5. The surgical robot according to claim 2, wherein the slave controller is configured to calculate the slave control value by a proportional control based on a difference between the surgical tool state and the target state, and wherein the surgical robot further comprises:

a display configured to display a gain of the proportional control; and an input device configured to receive an operation to change the gain of the proportional control that is displayed.

6. The surgical robot according to claim 5, wherein the slave controller is configured to calculate the slave control value by performing an integral control based on the difference between the surgical tool state and the target state, wherein the display is configured to display a gain of the integral control, and wherein the input device is configured to receive an operation to change the gain of the integral control that is displayed.

7. The surgical robot according to claim 1, wherein the slave controller is configured to calculate the slave control value by a proportional control based on a difference between the surgical tool state and the target state, wherein the master controller is configured to calculate the master control value by a proportional control based on the difference between the surgical tool state and the target state, and wherein a gain of the proportional control in the master controller is greater than a gain of the proportional control in the slave controller.

8. The surgical robot according to claim 1, wherein the master controller is configured to calculate the master control value by a proportional control based on a difference between the surgical tool state and the target state, and wherein the surgical robot further comprises:

a display configured to display a gain of the proportional control; and an input device configured to receive an operation to change the gain of the proportional control that is displayed.

9. The surgical robot according to claim 1, wherein the slave controller is configured to calculate the slave control value by a proportional control based on a difference between the surgical tool state and the target state, and wherein the surgical robot further comprises:

a display configured to display a gain of the proportional control; and an input device configured to receive an operation to change the gain of the proportional control that is displayed.

10. A controller for a surgical robot, the controller comprising:

a master controller configured to control a master, the master being configured to receive an operation from a user and to apply a reaction force to the user performing the operation and the master controller being configured to cause the reaction force to be generated; and a slave controller configured to control a slave based on a target state, the slave being configured to actuate a surgical tool, the target state being a state of the surgical tool based on the operation received by the master, and the slave controller being configured to cause the surgical tool to be actuated, wherein the slave controller is configured to calculate a slave control value based on a surgical tool state and the target state, the slave control value being for controlling the surgical tool, the surgical tool state being a state of the surgical tool detected by a slave detector, and the slave controller being configured to control the slave based on the slave control value, and wherein the master controller is configured to calculate a master control value based on the surgical tool state, the target state, and the slave control value obtained from the slave controller, the master control value being for controlling the reaction force and the master controller being configured to control the master based on the master control value.

11. The controller according to claim 10, wherein the slave controller is configured to calculate the slave control value by performing an integration based on the surgical tool state and the target state.

12. The controller according to claim 11, wherein the slave controller is configured to calculate the slave control value by a proportional control based on a difference between the surgical tool state and the target state, wherein the master controller is configured to calculate the master control value by a proportional control based on the difference between the surgical tool state and the target state, and wherein a gain of the proportional control in the master controller is greater than a gain of the proportional control in the slave controller.

13. The controller according to claim 11, wherein the master controller is configured to calculate the master control value by a proportional control based on a difference between the surgical tool state and the target state, wherein a gain of the proportional control is displayed on a display; wherein an operation to change the gain of the proportional control that is displayed is received, and wherein the master controller is configured to calculate the master control value according to the gain of the proportional control that is changed.

14. The controller according to claim 11, wherein the slave controller is configured to calculate the slave control value by a proportional control based on a difference between the surgical tool state and the target state, wherein a gain of the proportional control is displayed on a display; wherein an operation to change the gain of the proportional control that is displayed is received, and wherein the slave controller is configured to calculate the slave control value according to the gain of the proportional control that is changed.

15. The controller according to claim 14, wherein the slave controller is configured to calculate the slave control value by performing an integral control based on the difference between the surgical tool state and the target state, wherein a gain of the integral control is displayed on a display; wherein an operation to change the gain of the integral control that is displayed is received, and wherein the slave controller is configured to calculate the slave control value according to the gain of the integral control that is changed.

16. The controller according to claim 10, wherein the slave controller is configured to calculate the slave control value by a proportional control based on a difference between the surgical tool state and the target state, wherein the master controller is configured to calculate the master control value by a proportional control based on the difference between the surgical tool state and the target state, and wherein a gain of the proportional control in the master controller is greater than a gain of the proportional control in the slave controller.

17. The controller according to claim 10, wherein the master controller is configured to calculate the master control value by a proportional control based on a difference between the surgical tool state and the target state, wherein a gain of the proportional control is displayed on a display; wherein an operation to change the gain of the proportional control that is displayed is received, and wherein the master controller is configured to calculate the master control value according to the gain of the proportional control that is changed.

18. The controller t according to claim 10, wherein the slave controller is configured to calculate the slave control value by a proportional control based on a difference between the surgical tool state and the target state, wherein a gain of the proportional control is displayed on a display; wherein an operation to change the gain of the proportional control that is displayed is received, and wherein the slave controller is configured to calculate the slave control value according to the gain of the proportional control that is changed.

19. A surgical robot comprising:
a master configured to receive an operation from a user and to apply a reaction force to the user;
a master controller configured to control the master;
a slave configured to actuate a surgical tool;
a slave controller configured to control the slave to actuate the surgical tool according to a slave driving force; and
a slave detector configured to detect a surgical tool state of the surgical tool,
wherein the master controller and the slave controller are configured to perform asymmetrical bilateral control based on both proportional control and integral control.

20. The surgical robot according to claim 19, wherein the master controller calculates a master driving force for driving the master, based on a target state of the slave, a current state of the slave, and the slave driving force.

* * * * *